United States Patent
Uchiyama et al.

(10) Patent No.: US 10,098,915 B2
(45) Date of Patent: *Oct. 16, 2018

(54) EQUOL-PRODUCING LACTIC ACID BACTERIA-CONTAINING COMPOSITION

(71) Applicant: OTSUKA PHARMACEUTICAL CO., LTD., Tokyo (JP)

(72) Inventors: Shigeto Uchiyama, Miyaki-gun (JP); Tomomi Ueno, Kurume (JP); Toshimi Suzuki, Kurume (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1002 days.

This patent is subject to a terminal disclaimer.

(21) Appl. No.: 14/034,824

(22) Filed: Sep. 24, 2013

(65) Prior Publication Data

US 2014/0050703 A1 Feb. 20, 2014

Related U.S. Application Data

(63) Continuation of application No. 10/562,687, filed as application No. PCT/JP2004/009484 on Jun. 29, 2004.

(30) Foreign Application Priority Data

Jun. 30, 2003 (JP) ................................ 2003-187831

(51) Int. Cl.
| | |
|---|---|
| C12N 1/20 | (2006.01) |
| A61K 35/747 | (2015.01) |
| A23C 9/123 | (2006.01) |
| A23C 11/10 | (2006.01) |
| A61K 35/744 | (2015.01) |
| C12P 17/06 | (2006.01) |
| C12R 1/46 | (2006.01) |
| A23L 33/135 | (2016.01) |

(52) U.S. Cl.
CPC ............ *A61K 35/747* (2013.01); *A23C 9/123* (2013.01); *A23C 11/106* (2013.01); *A23L 33/135* (2016.08); *A61K 35/744* (2013.01); *C12P 17/06* (2013.01); *C12R 1/46* (2013.01); *A23Y 2220/00* (2013.01)

(58) Field of Classification Search
None
See application file for complete search history.

(56) References Cited

U.S. PATENT DOCUMENTS

| 7,396,855 B2 * | 7/2008 | Setchell | A23L 1/30 |
| | | | 514/456 |
| 8,765,445 B2 * | 7/2014 | Uchiyama | A23C 9/123 |
| | | | 424/93.45 |

FOREIGN PATENT DOCUMENTS

| JP | 2003-081855 A | 3/2003 |
| WO | 99/07392 A1 | 2/1999 |
| WO | 2004/009035 A2 | 1/2004 |
| WO | 2004/039327 A2 | 5/2004 |

OTHER PUBLICATIONS

Walther et al., Veterinary Microbiology 131 (2008) 348-357.*
Mehmeti et al., Food Control 53 (2015) 189e194.*
Supplemental European Search Report dated May 27, 2008 in EP 04746953.1.
Amir Zlotkin et al., "Identification of Lactococcus garvieae by PCR", Journal of Clinical Microbiology, 1998, 36(4): 983-985.
T. Ueno et al., "Identification of the Specific Intestinal Bacteria Capable of Metabolizing Soy Isoflavone to Equol, Poster 2.01.162", Ann. Ntr. Metab, 2001, 45: 114.
Motoi Tamura, et al, "Effects of Soy Protein-Isoflavone Diet on Plasma Isoflavone and Intestinal Microflora in Adult Mice", Nutrition Research, vol. 22, No. 6, Jun. 2002, pp. 705 to 713, ISSN0271-5317.
Motoi et al, Nutrition Research, 22(6):705-713 (2002).
Cai et al, J. Gen. Appl. Microbiol., 45:177-184 (1999).
Elliott et al, J. of Clin. Microbiol 29(12):2731-2734 (1991).
Villani et al, J. of Appl. Microbiology, 90:430-439 (2001).
Yoneya et al, Milk Science, 48(2):65-71 (1999).
Morishita et al., Journal of Diary Science vol. 82, No. 9, pp. 1897-1903, 1999.
Beasley et al., International Journal of Food Microbiology 81 (2003) pp. 159-162 (available on line Jul. 15, 2002).
Christine Paludan Muller et al., International Journal of Food Microbiology 73 (2002) 61-70.
Villani et al., Journal of Applied Microbiology 2001, 90, 430-439.
Fortina et al., Food Microbiology, vol. 20 (2003), pp. 397-404.

* cited by examiner

*Primary Examiner* — Irene Marx
(74) *Attorney, Agent, or Firm* — Sughrue Mion, PLLC

(57) ABSTRACT

An equol-producing lactic acid bacteria-containing composition comprises, as an essential component thereof, a lactic acid bacterial strain belonging to the genus *Lactococcus* having an ability to utilize at least one daidzein compound selected from the group consisting of daidzein glycosides, daidzein, and dihydrodaidzein to produce equol. Such a composition is effective for the prevention and alleviation of malaise inclusive of climacteric disturbance in middle-aged and elderly women for which no effective prophylactic method or alleviating means has heretofore been available.

3 Claims, 7 Drawing Sheets

EQUOL-PRODUCING LACTIC ACID BACTERIA-CONTAINING COMPOSITION

CROSS-REFERENCE TO RELATED APPLICATIONS

This is a Continuation of U.S. application Ser. No. 10/562,687 filed Dec. 28, 2005 (now U.S. Pat. No. 8,765,445), which is a National Stage Entry of PCT International Application No. PCT/JP2004/009484 filed Jun. 29, 2004, which claims benefit of Japanese Patent Application No. 2003-187831 filed Jun. 30, 2003. The above-noted applications are incorporated herein by reference in their entirety.

FIELD OF THE INVENTION

The present invention relates to equol-producing lactic acid bacterial strain, a composition comprising said lactic acid bacterial strain, and a method of producing equol by utilizing said lactic acid bacterial strain.

BACKGROUND OF THE INVENTION

It has heretofore been reported mostly in Europe and the United States of America that isoflavone (soy isoflavone) contained in soybeans has prophylactic efficacies (antiestrogen effect) in breast cancer, carcinoma of the prostate, and other diseases and that it has alleviating efficacies (estrogenic-like effect) in climacteric and postmenopausal osteoporosis, hyperlipidemia, hypertension, etc. (H. Adlercreutz et al., (1992) Lancet, 339, 1233; H. Adlercreutz et al., (1992) Lancet, 342, 1209-1210; D. D. Baird et al., (1995) J. Clin. Endocrinol. Metab., 80, 1685-1690; A. L. Murkies et al., (1995) Maturitas., 21, 198-195; and D. Agnusdei et al., (1995) Bone and Mineral., 19 (Supple), S43-S48).

Recently, however, doubts have been cast on the clinical efficacy of soy isoflavone and, instead, it is reported that equol as the active metabolite of soy isoflavone is a key factor in the expected efficacies in clinical application. Thus, several reports are available arguing that in breast cancer, carcinoma of the prostate, and climacteric and postmenopausal osteoporosis, the efficacy of soy isoflavone is surpassed by that of equol, the metabolite of soy isoflavone (D. Ingram et al., (1997) Lancet, 350, 990-994; A. M. Duncan et al., (2000) Cancer Epidemiology, Biomarkers & Prevention, 9, 581-586; C. Atkinson et al., (2002) J. Nutr., 32(3), 595S; H. Akaza et al., (2002) Jpn. J. Clin. Oncol., 32(8), 296-300; and S. Uchiyama et al., (2001) Ann. Nutr. Metab., 45, 113(abs)).

Moreover, many lectures were delivered on the subject of equol in the 4th International Symposium on the Role of Soy in Preventing and Treating Chronic Disease (San Diego, USA, 2001), and in December 2002 a comprehensive review of studies on equol was also reported. Thus, it is getting more or more accepted in academic circles that equol is the very entity of efficacies of soy isoflavone (K. D. R. Settchell et al., (2002) J. Nutr., 132, 3577-3584).

Furthermore, compared with soy isoflavone, equol is delivered to tissues such as the breast tissue and prostatic tissue with by far greater efficiency and, from this fact, the physiological significance of equol is endorsed (J. Maubach et al., (2003) J. Chromatography B., 784, 137-144; T. E. Hedlund et al., (2003) The Prostate, 154, 68-78).

Equol is produced by the intestinal flora and the involvement of individual difference in its production has been reported. It is also reported that equol producers among the Japanese account for about 50% (S. Uchiyama et al., (2001) Ann. Nutr. Metab., 45, 113 (abs)). Individuals who cannot produce equol are suspected to be lacking in equol-producing bacteria in their intestine. In such individuals, it is suspected that the expected antiestrogen and estrogenic-like effects may not be expected even if processed soybean foods are ingested. In order that the expected effects may be expressed in such individuals, it seems to be a reasonable course of action to have them ingest equol-producing bacteria or equol as such.

Based on the above idea, the inventors had conducted intensive investigations and isolated from human stools novel 3 strains of microorganisms and identified them: namely *Bacterioides* E-23-15 (FERM BP-6435), *Streptococcus* E-23-17 (FERM BP-6436), and *Streptococcus* A6G225 (FERM BP-6437), as equol producing-bacteria suitable for the expression of said antiestrogen and estrogenic-like effects, among other effects, and applied for a patent claiming inventions concerning these equol-producing strains of microorganisms and utilization of the microorganisms (WO99/07392).

DISCLOSURE OF INVENTION

The inventors conducted further studies and succeeded in the isolation and characterization of a lactic acid bacterial strain belonging to the genus *Lactococcus* which are capable of utilizing daidzein glycoside, daidzein, or dihydrodaidzein to produce equol as a novel strain of microorganism which is fundamentally different from the previously isolated and identified microorganisms. The present invention has been developed on the basis of the above isolation and identification of this novel strain of lactic acid bacterium.

The present invention subsumes the following inventions summarized in paragraphs 1-13.

Item 1. An equol-producing lactic acid bacteria-containing composition comprising, as an essential component thereof, a lactic acid bacterial strain belonging to the genus *Lactococcus* having an ability to utilize at least one daidzein compound selected from the group consisting of daidzein glycosides, daidzein, and dihydrodaidzein to produce equol.

Item 2. The composition according to Item 1, wherein said lactic acid bacterial strain belonging to the genus *Lactococcus* is *Lactococcus garvieae*.

Item 3. The composition according to Item 2, wherein said lactic acid bacterial strain belonging to *Lactococcus* is *Lactococcus* 20-92 deposited under FERM BP-10036.

Item 4. The composition according to Item 1 further comprising at least one member selected from the group consisting of daidzein compounds and daidzein compound-containing ingredients.

Item 5. The composition according to Item 4, wherein the daidzein compound-containing ingredient is soybean flour or soy milk.

Item 6. The composition according to Item 4 which is in the form of a beverage or a milk product.

Item 7. The composition according to Item 4 further comprising equol.

Item 8. The composition according to Item 7 which is in the form of a fermentation product of soy milk.

Item 9. A method of producing equil comprising the step of letting a lactic acid bacterial strain belonging to the genus *Lactococcus* having an ability to utilize a daidzein compound to produce equol act on at least one member selected from the group consisting of daidzein compounds and daidzein compound-containing ingredients.

Item 10. The method according to Item 9, wherein said lactic acid bacterial strain belonging to the genus *Lactococcus* is *Lactococcus garvieae*.

Item 11. The method according to Item 10 wherein said lactic acid bacterial strain belonging to the genus *Lactococcus* is *Lactococcus* 20-92 deposited under FERM BP-10036.

Item 12. The method according to Item 9, wherein the daidzein compound-containing ingredient is soybean flour or soy milk.

Item 13. A lactic acid bacterial strain belonging to the genus *Lactococcus* as deposited under FERM BP-10036.

The equol-producing lactic acid bacteria-containing composition of the invention described in detail bellow.

(1) The Lactic Acid Bacterial Strain Belonging to the Genus *Lactococcus*

The equol-producing lactic acid bacteria-containing composition of the invention comprises, as an essential component thereof, lactic acid bacterial strain belonging to the genus *Lactococcus* having an ability (metabolic activity) to utilize at least one daidzein compound selected from the group consisting of daidzein glycosides, daidzein, and dihydrodaidzein and thereby produce equol.

A specific example of said lactic acid bacterial strain is *Lactococcus* 20-92 (FERM BP-10036) which the inventors isolated from human stools and identified de novo.

The bacteriological characteristics of the lactic acid bacterial strain are described in detail bellow.

I. State of Growth on the Medium

This strain shows good or normal growth on EG (Eggerth-Gagnon) agar, BL (Blood Liver) agar, and GAM (Gifu Anaerobic Medium) when cultured anaerobically in an anaerobic jar with steel wool at 37° C. for 48 hours or cultured aerobically at 37° C. for 48 hours. The colonial morphology is raised in a circular or convex manner, with both the surface and peripheral edge being smooth, and assumes a gray-white color on EG agar and a tan-brown color on BL agar. Morphologically, it is a Gram-positive diplococcus. This strain is not sporogenic.

II. Biochemical Characteristics (1) Optimum temperature for growth: 37° C.
(2) Optimum pH for growth: 7.0
(3) Liquefaction of gelatin: −
(4) Production of acetoin from pyruvic acid: +
(5) Hydrolysis of hippuric acid: −
(6) Hydrolysis of esculin: +
(7) Pyrrolidonyl arylamidase: +
(8) α-Galactosidase: −
(9) β-Galactosidase: −
(10) β-Glucronidase: −
(11) Alkaline phosphatase: −
(12) Leucine arylamidase: +
(13) Arginine dihydrase: +
(14) Assimilation of carbon sources
  D-Ribose +
  L-Arabinose −
  D-Mannitol +
  D-Sorbitol −
  Lactose −
  D-Trehalose +
  Inulin −
  D-Raffinose −
  Starch +
  Glycogen −

(15) Organic Acid Composition after Utilization of Peptone or Glucose

Using PYF (peptone-yeast extract Fields) medium (peptone content: ca 5%) used as sugar utilization medium and PYF medium supplemented with glucose at a final concentration of 0.5%, the strain of the invention was cultured aerobically at 37° C. for 72 hours and the organic acids in the cultures were assayed by HPLC. The results (unit: mM) are presented below in Table 1

TABLE 1

| Organic acid | Peptone | Glucose |
| --- | --- | --- |
| Maleic acid | nd | nd |
| Succinic acid | 0.00 | 0.01 |
| Lactic acid | 3.33 | 27.35 |
| Formic acid | 1.13 | 0.88 |
| Acetic acid | 3.32 | 0.57 |
| Pyroglutamic acid | 0.12 | 0.25 |
| Propionic acid | nd | nd |
| i-Butyric acid | nd | nd |
| n-Butyric acid | nd | nd |
| i-Valeric acid | nd | nd |
| n-Valeric acid | nd | nd | nd = not detected

From the above cultural and biochemical characteristics, the strain of the invention is classified into *Lactococcus garvieae* which is a gram-positive coccus but differs from its type strain (Schleifer, K. H., Kraus, J., Dvorak, C., Kilpper-Balz, R., Collins, M. D. and Fischer, W. Transfer of *Streptococcus lactis* and related *streptococci* to the genus *Lactococcus* gen. nov. Syst. Appl. Microbiol., 6, 183-195, 1985; ATCC43921 (JCM10343) and ATCC49156 (JCM8735)) in the utilization of starch.

Therefore, the inventors named this strain *Lactococcus* 20-92 and deposited it with the National Institute of Advanced Industrial Science and Technology International Patent Organism Depositary, AIST Tsukuba Central 6, 1-1, Higashi 1-Chome Tsukuba-shi, Ibaraki-ken 305-8566, Japan as of Jan. 23, 2003, under the accession number of FERM P-19189. This microorganism is now placed under Budapest Treaty deposit, and the accession number is FERM BP-10036.

This strain was found to assimilate glucose and, then, elaborate lactic acid (L-lactic acid), verifying that it is a member of homofermentative lactic acid bacteria.

Furthermore, sequencing of the 16SrRNA of this strain revealed 99.189% homology with the type strain *Lactococcus garvieae* (JCM10343) and 99.375% homology with *Enterococcus seriolicida*, JCM8735).

Incidentally, since *Enterococcus seriolicida* referred to above was akin to *Lactococcus garvieae* in DNA-DNA homology analysis, it was reclassified into *Lactococcus garvieae* in 1996. Therefore, *Lactococcus garvieae* has two type strains (JCM8753 strain and 10343 strain) which are dissimilar in origin. *Enterococcus seriolicida* (JCM8735) was derived from the kidney of infected yellowtail and the intrinsic *Lactococcus garvieae* (JCM10343) was derived from bovine mastitis.

To explore the relative homology of *Lactococcus* 20-92 with the above two type strains, a phenotypic comparison was made. The results are presented below in Table 2.

TABLE 2

| Characteristics | Strain of invention | JCM10343 | JCM8735 |
|---|---|---|---|
| Deamination (Arg → NH₃) | ± | ± | ± |
| Temperature dependence of growth | | | |
| 10° C. | + | + | + |
| 15° C. | + | + | + |
| 30° C. | + | + | + |
| 37° C. | + | + | + |
| 40° C. | + | + | − |
| 45° C. | − | − | − |
| pH dependence of growth | | | |
| pH4.5 | ± | ± | ± |
| pH7.5 | + | + | + |
| pH9.6 | + | + | + |
| Salt tolerance (NaCl) | | | |
| 6.5 | + | + | + |
| Peptidoglycan | Lys-Ala-Gly | Lys-Ala-Gly | Lys-Ala-Gly |
| Quinone type | MK-8,9 | MK-8,9 | No quinone |

MK denotes menaquinone

It will be apparent from Table 2 that the present strain *Lactococcus* 20-92 was in agreement with the type strain (JCM10343) of *Lactococcus garvieae* in phenotype but was different from the type strain (JCM8735) of *Enterococcus seriolicida* in growth behavior at 40° C. and in the production or non-production of quinone. Accordingly the present strain was judged to be akin to *Lactococcus garvieae* (JCM10343).

The present strain *Lactococcus* 20-92 can be classed among Milk-cultured *Lactococci* in the GRAS [acronym of Generally Recognized As Safe list by FDA (Food and Drug Administration, U.S.A.)] and its safety as a food is considered to be high.

With regard to *Lactococcus garvieae*, there is not a report ever suggesting its pathogenicity to human beings and there is no production of virulent substances such as toxins, either, so that this bacterial species is generally acknowledged to be a species of high safety.

Moreover, *Lactococcus garvieae* has so far been detected in mozzarella cheese, raw milk, processed meat products under low-temperature storage, plaa-som (a fermented fish product widely consumed in Thailand), and Toma Piemontese cheese which is an artisanal protected denomination origin (PDO) Italian cheese, i.e. traditional cheese in Italy, among others, and reportedly this microorganism is detected at a high incidence of the order of $10^5$ cells/gram from plaa-som and $10^8$ cells/gram from Toma Piemontese cheese, but this food has a long history of eating assuring the safety of this organism. (P-M. Christine et al., (2002) Int. J. Food Microbiol., 73, 61-70; M. G. Fortina, et al., (2003), Food Microbiol., 20, 379-404).

On the other hand, *Enterococcus seriolicida* is reportedly pathogenic to cultured fishes such as yellowtail. Since *Lactococcus* 20-92, which is, thus, a strain of *Lactococcus garvieae*, is considered to be phylogenetically related to *Enterococcus seriolicida*, there was an apprehension of its pathogenic potential to cultured fishes. However, the studies by the inventors comparing the electronmicrograph of *Lactococcus* 20-92 with that of the pathogenic counterpart (*Enterococcus seriolicida* KG) revealed that unlike said pathogenic strain, the strain of the invention has no capsule on the cell surface. Therefore, the present strain is considered to have no pathogenicity, nor does it present with an ecological contamination problem. This conclusion is also corroborated by the description in the following literature. Thus, Yoshida et al. argue about the pathogenicity of microbial cells to cultured fishes that a capsule present on the cell surface inhibits phagocytosis by macrophages, with the result that the particular bacteria are not killed but septicemia is induced systemically in cultured fishes infected with the bacteria (T. Yoshida, et al., (1996) Dis. Aquat. Org., 25, 81-86).

Furthermore, the present strain *Lactococcus* 20-92 retains the desired equol-producing ability (activity) even in the case of direct fermentation in milk and has the characteristic that for the maintenance of this equol-producing ability, no special culture medium is required. Thus, by carrying out a fermentation in soy milk as used alone, the strain utilizes daidzein compounds in the soy milk to elaborate equol.

Heretofore, there is no report available on lactic acid bacteria of the genus *Lactococcus* which ever have such an equol-producing ability. Therefore, the present invention further provides a novel strain of lactic acid bacterium having such an equol-producing ability.

(2) Daidzein Compounds and Daidzein Compound-containing Ingredients

Daidzein compounds, which are utilized by the present strain *Lactococcus* 20-92, include a daidzein glycoside, daidzein, and dihydrodaidzein. A specific example of said daidzein glycoside is daidzin. Daidzin is an isoflavone glycoside having daidzein as the aglycone (daidzein glycoside). Referring to daidzin, it is utilized by said strain of microorganism to liberate daidzein which is further utilized by the strain to give dihydrodaidzein, from which equol is finally produced.

In the present invention, said daidzein compound is used as the substrate. The substrate includes not only daidzein compounds but also various materials or ingredients containing the same. As a representative example of said material or ingredient containing said daidzein compounds (referred to as daidzein compound-containing ingredient), soy isoflavone can be mentioned. Soy isoflavone is already available from commercial sources and, in the present invention, such commercial products, for example "Fujiflavone P10" (registered trademark) from Fujicco Co., Ltd., can be used. Moreover, said daidzein compound-containing ingredient includes not only soy isoflavone but also plant tissues as such, e.g. kudzu(=*Pueraria thurbergiana* Benth) and root of kudzu (arrowroot), red clove, alfalfa, etc., and isoflavone derivatives originating therefrom.

Further examples of said daidzein compound-containing ingredient includes not only the above-mentioned food materials such as soybean, kudzu, root of kudzu, red clove, alfalfa, etc. but also processed products thereof, such as soybean meal (soybean flour), boiled soybeans, tofu (soybean curd), fried bean curd, soy milk, soybean hypocotyl extract, etc., fermentation products thereof, such as natto (fermented soybeans), soy sauce, miso, tempeh, and fermented soy beverages. These materials invariably contain daidzein compounds. Moreover, these not only contain daidzein compounds but also estrogenic isoflavones, such as genistein and its glycosides (genistin etc.); glycitein and its glycosides (glycitin etc.); biochanin A and formononetin which are partially methylated daidzein and genistin precursors and can be used with advantage in the present invention.

(3) Composition of the Invention
(3-1) An Equol-Producing Lactic Acid Bacteria-containing Composition The equol-producing lactic acid bacteria-containing composition of the invention comprises, as an essential component thereof, acetic acid bacterial strain belonging to the genus *Lactococcus* having an ability to act on the substrate daidzein compound or daidzein-containing ingredient to produce equol, with the above-mentioned *Lactococcus* 20-92 being a representative example. The lactic acid bacterial strain for use as said essential component usually are viable bacterial strain but are not limited to these but may be any of its cultures, crude or purified preparations of such cultures, which contains isolated cells, and lyophilizates thereof.

The cultures of said bacterial strain can be obtained typically by the procedure comprising culturing the strain in a medium suited for its growth, for example MRS medium, at 37° C. for about 48 hours. Following the cultivation, the cells can be recovered by, for example, centrifuging the culture at 3,000 rpm (4° C.) for 10 minutes. These can be purified in the conventional manner. Moreover, these cells can be lyophilized. The resulting lyophilizates can also be utilized as the active component of the composition of the invention.

All that is necessary for the composition of the invention is that it contains the bacteria (cells or equivalent) as said active component but, if desired, the composition may be supplemented with nutrients suited for the maintenance (or growth) of the microorganism as said active component. The nutrients mentioned above may for example be the nutrient media for culture of the respective microorganisms, such as BHI, EG, BL and GAM, as mentioned hereinbefore.

Examples of the other nutrients include various oligosaccharides, such as lactooligosaccharide, soy oligosaccharide, lactulose, lactitol, fructooligosaccharide, and galactooligosaccharide. The amount of such oligosaccharides is not particularly restricted but is preferably selected from a range such that the final concentration thereof in the composition of the invention will be about 1-3 weight %.

The above composition of the invention, when taken orally, expresses the desired equol-producing activity in the recipient's body. Generally the Japanese have the habit to eat daidzein compound-containing foods, typically the above-mentioned food materials or ingredients, e.g. soybeans, secondary products thereof, and fermentation products thereof and, therefore, the intake of the composition of the invention results in the production of equol in vivo.

Furthermore, where necessary, the composition of the invention may be supplemented with suitable amounts of various vitamins, trace metal elements, and so forth. Examples of said vitamins include vitamin B, vitamin D, vitamin C, vitamin E, and vitamin K [particularly MK-7 (menaquinone-7) derived from *Bacillus natto*]. Examples of said trace metal elements are zinc, selenium, iron, manganese, etc.

The quantity of the microorganism to be formulated in the composition of the invention can be judiciously selected according to the kind of bacterial strain used. Taking *Lactococcus* 20-92 as an example, the number of organisms (viable cell count) is preferably adjusted to about $10^8$~$10^9$ cells/100 g composition. The viable cell count is determined as follows. A sample dilution is coated onto an agar medium for bacterial culture and cultured aerobically at 37° C. and the colonies formed are counted. The quantity of the microorganism described above can be judiciously adjusted according to the form of the composition to be prepared using the above-mentioned quantity as a reference.

(3-2) The Daidzein Compound-containing Composition of the Invention

The composition of the invention may further contain, if necessary, at least one member selected from the group consisting of the aforementioned diadzein compounds and daidzein compound-containing ingredients. Among various kinds of daidzein compound and daidzein compound-containing ingredient, soybean hypocotyls and food ingredients prepared starting with the hypocotyls, are particularly preferred, and, among these, water-soluble or emulsified food ingredients are still more preferred. Among other preferred examples of said daidzein compound-containing ingredient are soybean flour and soy milk.

Due to the substrate contained in the formulation, a person not accustomed to eating soybeans and the like food ingredients can take the composition orally, and the ingested microorganism utilizes the formulated substrate to produce the objective equol in the body.

The amount of said daidzein compound and/or daidzein compound-containing ingredient in the composition is not particularly restricted but may reasonably be about 10-25 mg which is equivalent to the usual daily intake by the average Japanese.

(3-3) Equol-containing Composition of the Invention

The composition of the invention may further contain equol.

Generally, one's appetite for a food is whetted when the food material is caused to undergo lactic acid fermentation, for instance. Moreover, *Lactococcus* 20-92, which is a representative example of microorganism for use in the composition of the invention, has a very high equol-producing ability (activity). The present invention further provides an equol-containing composition, such as fermented soy milk, which is prepared by permitting said strain of microorganism to act on a daidzein compound-containing ingredient such as soy milk, and thereby let it utilize the daidzein compound in the soy milk to elaborate equol.

As the substrate for use in this aspect of the invention, the above-mentioned various kinds of daidzein compound and daidzein compound-containing ingredient can be employed. Among these, solutions or emulsions prepared from soy milk, soy flour or the like are preferred.

A preferred specific example of the equol-containing composition of the invention is the fermentation product obtained by a process which comprises adding soy isoflavone or a food material containing it to a suitable medium and culturing the microorganism of the invention, preferably *Lactococcus* 20-92, therein to cause fermentation. More particularly, such fermentation can be effected by the procedure which comprises adding a predetermined amount of the microorganism of the invention to a mixture of a sterilized substrate solution and a nutrient medium favorable for growth of the microorganism, such as BHI, EG, BL or GAM, or to cow's milk, soy milk, or a vegetable juice which can be used as food, and carrying out an anaerobic or aerobic fermentation reaction at 37° C. under stationary conditions for about 48-96 hours [where necessary, a pH control agent and a reducing agent (e.g. yeast extract, vitamin $K_1$, or the like) may be added]. In the above procedure, the amount of the substrate may be about 0.01-0.5 mg/ml, and the inoculum size of the microorganism can be selected from the range of about 1 to about 5%.

In this manner, the equol-containing composition of the invention can be produced. This composition can be applied with advantage in the above-described form of a fermentation product as a food or a pharmaceutical product. Moreover, the produced equol can be isolated and purified from the culture broth or fermentation product in the per se known manner, optionally formulated with suitable amounts of other food ingredients or the like, and processed into suitable food forms or pharmaceutical product forms.

The isolation and purification referred to above can be achieved by, for example, adsorbing the fermentation product on an ion exchange resin (DIAION HP20, product of Mitsubishi Kasei Corporation), eluting it with methanol, and concentrating the eluate to dryness.

The amount of equol in the composition of the invention is selected according to the form of food or pharmaceutical product to be produced and is not particularly restricted. Preferably, however, the amount should generally be such that about 2-5 mg of equol will be contained in each 100 g of the total composition.

The presence of equol in the product composition of the invention can be confirmed by the method described hereinafter in Test Example 1.

The equol-containing composition of the invention ranks high on the safety scale because the active ingredient equol is a naturally-occurring substance. Moreover, because it is prepared by using the lactic acid bacterial strain, the risk of contamination with chemicals originating from the production line is low. As additional advantages, high yield and low cost as well as savory taste and flavor as food can be mentioned.

(3-4) Forms of Food

The equol-producing lactic acid bacteria-containing composition of the invention is generally processed into food forms comprising the particular lactic acid bacterial strain as an essential component in combination with a suitable edible carrier.

Specific food forms of the composition of the invention include the beverage form, milk product form other than said beverage form (inclusive of fermented milk form), solid food form, cell-containing microencapsulated form, and so forth. The composition of the invention in the beverage form includes lactic acid bacteria beverages and lactic acid bacteria-containing beverages.

The terms "fermented milk" and "lactic acid bacteria beverage" as used herein are in conformity with the definitions in Article 2-37 "Fermented Milk" and Article 2-38 "Lactic Acid Bacteria Beverage" of the "Regulations relating to the Ingredients etc. of Milks and Milk Products" of the former Ministry of Health and Welfare. Thus, "fermented milk" means a pasty or liquid preparation resulting from the fermentation of a milk or a milk (dairy) product with lactic acid bacteria or yeasts. Therefore, the "fermented milk" includes not only products of beverage form but also products of yogurt form. The "lactic acid bacteria beverage" means a beverage prepared by using a pasty or liquid product resulting from the fermentation of a milk or a milk product with a lactic acid-fermenting bacterium or yeast as a chief material and diluting it with water.

The lactic acid bacteria-containing beverage includes fermented vegetable drinks, fermented fruit drinks, and fermented soy milk drinks etc. Examples of items in the form of milk products other than the beverage form includes products of the curd form such as yogurt. The solid food form includes granules, powders (inclusive of e.g. freeze-dried powders of fermented milk), tablets, effervescent tablets, gums, gumdrops, and puddings etc.

Processing into these forms can be carried out in the conventional manner. Moreover, the carrier for use in the processing into such forms may be any edible carrier. Particularly preferred carriers are those having good mouth-feel and taste-improving effects. Examples of such carriers having good mouth-feel and taste-improving effects include artificial sweeteners, sorbitol, xylitol, and so on. Other preferred carriers are, for example, masking agents such as trehalose (product of Hayashibara), cyclodextrin, Benekote BMI (product of Kao Corporation), etc.

The lactic acid bacteria-containing beverage as a preferred specific food form is described in detail below. Processing into such a beverage can be carried out by the procedure which comprises culturing the microorganism in a suitable fermentation material containing nutrients for the microorganism, such as fluids derived from vegetables or fruits, soy-milk (emulsified soy), etc. to thereby cause fermentation of said material. The vegetables and fruits for use as the fermentation material include cuttings, crushings, grindings, squeezed-out juices, enzyme-treated products, and dilutions or concentrates thereof. The vegetables include pumpkins, carrots, tomatoes, sweet peppers, celery, spinach, pigmented sweet potatoes, corn, beats, kale, parsley, cabbages, and broccoli etc. The fruits include apples, peaches, bananas, strawberries, grapes, water melons, oranges, and mandarin oranges etc.

The cuttings, crushings, and grindings of vegetables and fruits can be obtained by, for example, the procedure which comprises washing the vegetable or fruit, subjecting it to a blanching treatment, e.g. placing in hot water, where necessary, and cutting, pulverizing or milling it by means of a crusher, mixer, food processor, pulper finisher, Mycolloider, or the like. Juices can be prepared by using a filter press, juicer-mixer, or the like. Juices can also be prepared by filtering said grindings (millings) through a filter cloth or the like. The enzyme-treated products can be prepared by permitting cellulase, pectinase, protopectinase or the like to act upon said cuttings, crushings, grindings, or juices. The dilutions include 1 to 50-fold aqueous dilutions. The concentrates include those concentrated 1 to 100-fold by such means as freeze concentration, concentration under reduced pressure, etc.

Soy milk which is another specific example of the fermentation substrate material can be prepared from soybean materials in the routine manner. The soy milk includes a homogenate prepared by immersing skinned soybeans in water, wet-pulverizing these soybeans with a suitable mill or the like, and homogenizing the pulverizate in the routine manner and a solution of water-soluble soy protein in water etc.

The fermentation using a microorganism can be carried out by inoculating said fermentation substrate material with the microorganism of the invention and incubating the inoculated material under stationary conditions. The medium may optionally be supplemented with fermentation-promoting substances insuring good growth of the microorganism used, for example various carbon sources such as glucose, starch, sucrose, lactose, dextrin, sorbitol, fructose, etc., nitrogen sources such as yeast extract, peptone, etc., vitamins, and minerals.

The inoculum size of the microorganism should be generally equivalent to a viable cell count of not less than about $1\times10^6$ cells, preferably about $1\times10^7$ cells per cubic centimeter of the fermentation substrate fluid. As regards cultural conditions, the fermentation temperature is generally selected from the range of about 20-40° C., preferably about 25-37° C., more preferably 37° C. and the fermentation time is selected from the range of about 8-24 hours.

For stable fermentation, it is recommendable to prepare a starter in advance and inoculate the fermentation substrate material with the starter for fermentation. The representative starter may for example be culture obtained by inoculating the present strain of microorganism of the invention into said fermentation substrate material subjected to usual sterilization at 90-121° C. for 5-20 minutes beforehand, yeast extract-supplemented 10% skim milk powder, or the like and cultivating the microorganism under the same conditions as above. The starter thus prepared usually contains about $10^7$-$10^9$ cells of the microorganism of the invention per gram of the culture.

The lactic acid fermentation product obtained in the above manner may at times be a curd form (a yogurt-like or pudding-like form) and such a product can be directly taken as a food. The lactic acid fermentation product in said curd form can be further homogenized to prepare the desired beverage form (for example, a fermented soy milk beverage). This homogenization can be carried out using an ordinary homogenizer. More particularly, it can be carried out using Gaulin's high-pressure homogenizer [LAB 40] at about 200-1000 kgf/cm$^2$, preferably about 300-800 kfg/cm$^2$, or a Sanwa Machine Industry Co.'s homogenizer (article number: HA x 4571, H20-A2 etc.) at not less than 150 kg/cm$^2$. By this homogenization, a beverage product, particularly a fermented soy milk beverage, which has an excellent palatability, particularly a smooth mouth-feel, can be obtained. In carrying out said homogenization, it is permissible, where necessary, to make appropriate diluting, add an organic acid for pH adjustment, and/or add various additives which are usually employed in the manufacture of beverages, such as sugars, fruit juices, viscosity builders, surfactants, and flavors, in suitable amounts. As a specific preferred example of each kind of additive mentioned above and its addition level (% by weight based on the weight of the curd-form fermentation product) are: glucose 8% (% by weight, the same applies hereinafter), sugar 8%, dextrin 8%, citric acid 0.1%, glycerol fatty acid ester 0.2%, and flavor 0.1%.

Thus obtained lactic acid bacteria beverage of the invention such as a fermented soy milk beverage can be aseptically dispensed into suitable containers in the conventional manner to provide the end-product. This product has a good palatability allowing smooth swallowing and a good flavor.

The dosage (intake amount) of the above product can be judiciously selected according to the age, sex, body weight, and severity of illness of the recipient, among other variables, and is not particularly restricted. Generally, 100-300 mL of a beverage product with a viable cell count of $10^8$-$10^9$ cells/mL can be ingested per day.

A further specific example of the composition of the invention in the food form is the effervescent tablet form. This form can be prepared by formulating 10-35% (% by weight; the same applies below) of sodium carbonate and/or sodium hydrogencarbonate and 20-70% of a neutralizer, as effervescent ingredients, with 0.01-50% of the bacteria (lyophilized cells) of the invention. The neutralizer to be used in this manner is an acidic compound capable of neutralizing said sodium carbonate and/or sodium hydrogencarbonate to generate carbon dioxide gas. Representative examples of said neutralizer are organic acids such as L-tartaric acid, citric acid, fumaric acid and ascorbic acid.

The amount of said effervescent ingredients in the effervescent product of the invention is such that when this product of the invention is dissolved in water, the solution shows acidity, particularly an acidity of pH about 3.5-4.6. More particularly, the amount can be selected from the range of 10-35% sodium carbonate and/or sodium hydrogencarbonate and 20-70% neutralizer. Particularly, the amount of sodium carbonate is selected from the range of 11-31%, preferably 22-26%; sodium hydrogencarbonate from the range of 10-35%, preferably 20-30%. Among these alternative choices, it is most preferable to use sodium hydrogencarbonate alone within the range of 20-25%. The amount of the neutralizer is selected from the range of 20-70%, preferably 30-40%. In particular, it is most preferable to use L-tartaric acid within the range of 20-25% and ascorbic acid within the range of 8-15%.

The effervescent product contains the microorganisms of the invention and the effervescent ingredients as essential components and may optionally be contained suitable amounts of various known additives such as the excipient, binder, disintegrator, lubricant, viscosity builder, surfactant, osmolarity modulating agent, electrolyte, sweetener, flavor, colorant, pH control agent, and so forth. Examples of the additives are starches such as wheat starch, potato starch, corn starch, dextrin, etc.; saccharides such as sucrose, glucose, fructose, maltose, xylose, lactose, etc.; sugar alcohols such as sorbitol, mannitol, maltitol, xylitol, etc.; sugar rearrangement glycosides such as coupling sugar, palatinose, etc.; excipients such as calcium phosphate, calcium sulfate, etc.; binders/thickeners such as starches, saccharides, gelatin, gum Arabic, dextrin, methylcellulose, polyvinylpyrrolidone, polyvinyl alcohol, hydroxypropylcellulose, gum xanthan, pectin, gum tragacanth, casein, alginic acid, etc.; lubricants such as leucine, isoleucine, L-valine, sugar esters, hydrogenated oils, stearic acid, magnesium stearate, talc, macrogols, etc.; disintegrators such as crystalline cellulose (Avicel, Asahi Chemical Industry Co., Ltd.), carboxymethylcellulose (CMC), carboxymethylcellulose sodium (CMC-Na), carboxymethylcellulose calcium (CMC-Ca), etc.; surfactants such as polyoxyethylene sorbitan fatty acid ester (polysorbate), lecithin, etc.; dipeptides such as aspartame, alitame, etc.; and sweeteners such as stevia, saccharin, and so forth. These can be judiciously selected and used in suitable amounts taking into consideration the relationship of each to the essential components, the proportion of the preparation, and method of production of the preparation, among other factors.

Furthermore, in the effervescent preparation of the invention, vitamins, particularly cyanocobalamine and ascorbic acid (vitamin C), can be formulated in suitable amounts. The amount is not particularly restricted but usually vitamin C, for instance, may be added up to 30% at the maximum, preferably within the range of about 5-25%.

The method of producing the effervescent preparation of the invention can be fundamentally similar to the conventional method for production of effervescent tables of this kind. Thus, the preparation of the invention in the effervescent tablet form can be prepared by weighing out predetermined amounts of the respective ingredients, mixing them, and processing the whole by the direct powder compression method or the dry or wet granulation-compression method, for instance.

The preparation of the invention, thus obtained, can be converted to a beverage form suitable for oral administration by mere placing in water and be administered orally.

The dosage (intake amount) thereof can be judiciously established according to the age, sex, body weight, severity of illness of the recipient, among other variables, and is not particularly restricted but generally 1-2 tablets of the effervescent tablet form of the invention weighing about 1.5-6.0 g per tablet can be dissolved in 100-300 mL of water and caused to be ingested per dose.

The particularly preferred blending proportions of the substrate daidzein compound or daidzein compound-containing ingredient, the particular lactic acid bacterial strain, and optionally formulated other ingredients in the composition of the invention, per 100 g of the composition, are: the daidzein compound or daidzein compound-containing ingredient within the range of about 10-50 mg calculated as daidzein, the number of the lactic acid bacterial strain within the range of $10^9$-$10^{10}$ cells (viable cell count), and oligosaccharides and others within the range of about 1-5 g.

Since the equol-producing lactic acid bacteria-containing composition of the invention is designed to contain a microorganism (primarily live bacteria) as mentioned hereinbefore, such conditions as the application of heat and pressure are not recommendable in the processing of the composition into end products. Therefore, in processing the composition of the invention into such product forms as bars, granules, powders, and tablets, it is preferable to directly formulate the microorganism in the form of lyophilized cells or use lyophilized cells treated with a suitable coating agent.

However, the equol-producing lactic acid bacteria-containing composition of the invention need not essentially contain viable bacteria. When said composition comprising viable bacteria and said daidzein compound or the like which said bacteria may utilize contains bacteria-produced equol, it may be subjected to a routine heat sterilization to kill the bacteria. Such a heat sterilization given to the composition inhibits taste and flavor deteriorations caused by excessive fermentation of the viable bacteria formulated in the composition during storage or distribution on the market.

(3-5) Pharmaceutical Product Forms

The equol-producing lactic acid bacteria-containing composition of the invention can be processed into pharmaceutical preparations generally containing said defined lactic acid bacterial strain as an essential component together with a suitable pharmaceutically acceptable carrier.

The carrier includes various diluents and excipients, such as fillers, volume builders, binders, humectants, disintegrators, surfactants, lubricants, etc. which are known to be used in the art. These can be selectively used according to the unit dosage form of the preparation.

As the unit dosage form of the pharmaceutical preparation, a variety of forms can be selectively used. The representative forms are tablets, pills, powders, solutions, suspensions, emulsions, granules, capsules, and suppositories.

The carrier which can be used in the processing into the tablet form includes various excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solution, starch solution, gelatin solution, carboxymethylcellulose, hydroxypropylcellulose, methylcellulose, polyvinylpyrrolidone, etc.; disintegrators such as carboxymethylcellulose sodium, carboxymethylcellulose calcium, low-substituted hydroxypropylcellulose, dry starch, sodium alginate, agar powder, laminaran powder, sodium hydrogencarbonate, calcium carbonate, etc.; surfactants such as polyoxyethylene-sorbitan fatty acid esters, sodium lauryl sulfate, stearic acid monoglyceride, etc.; disintegration inhibitors such as sucrose, stearin, hydrogenated cacao butter, hydrogenated oils, etc.; absorption promoters such as quaternary ammonium bases, sodium lauryl sulfate, etc.; humectants such as glycerol, starch, etc.; adsorbents such as starch, lactose, kaolin, bentonite, colloidal silica, etc.; and lubricants such as purified talc, stearates, boric acid powder, polyethylene glycol, and so forth.

Furthermore, where necessary, tablets may be prepared in the forms having the conventional coatings such as sugar-coated tablets, gelatin-coated tablets, enteric-coated tablets, film-coated tablets, etc., or in the form of double-layered tablets or multi-layered tablets.

The carrier which can be used in the formation of pills includes various excipients such as glucose, lactose; starch, cacao butter, hydrogenated vegetable oils, kaolin, talc, etc.; binders such as gum Arabic powder, gum tragacanth powder, gelatin, ethanol, etc.; and disintegrators such as laminaran, agar, and so forth.

The carrier which can be used in the formation of suppositories includes polyethylene glycol, cacao butter, higher alcohols, higher alcohol esters, gelatin, and semi-synthetic glycerides etc. The encapsulated product can be manufactured generally by blending the bacteria of the invention with various kinds of pharmaceutical carriers such as those mentioned above and filling the mixture into hard capsule shells or soft elastic capsule shells in the conventional manner.

Furthermore, where necessary, colorant, preservative, flavoring, corrigent, sweetener, and other drugs can be incorporated into the pharmaceutical product of the invention.

The quantity of the microorganism of the invention to be incorporated in the preparation of the invention is not particularly restricted but can be judiciously selected from a broad range. The generally recommended proportion is about $10^8$-$10^{10}$ cells/g of the pharmaceutical preparation.

The method of administration of the above pharmaceutical preparation is not particularly restricted but can be established according to the preparation forms, various patient factors such as age, sex, etc. and the severity of illness. For example, the tablets, pills, solutions, suspensions, emulsions, granules, and capsules are administered orally and the suppositories are administered rectally.

The dosage of said pharmaceutical preparation can be judiciously established according to the method of administration, the patient's age, sex and other factors, and the severity of illness but is preferably about 0.5-20 mg/day in terms of the microorganism of the invention, i.e. active ingredient, per kg body weight. This preparation can be administered in 1-4 divided doses a day.

On ingestion (administration) of the composition of the invention, the microorganism in the composition finds its way alive into the lower digestive tract or settles there as part of the intestinal flora, whereby the expected efficacy is expressed. In this connection, the particularly preferred preparation form is the enteric-coated tablet, with which the microorganism can be transported to the intestines without being attacked by gastric acid.

The equol-producing lactic acid bacteria-containing composition of the invention as obtained in the above manner is useful for the symptomatic prophylaxis and treatment of malaise and/or postmenopausal osteoporosis and climacteric disturbances in middle-aged and elderly women. Such prophylaxis and treatment can be accomplished by administering an effective amount of said composition of the invention to the middle-aged or elderly woman for whom it is required or causing them to ingest the same. The effective amount mentioned just above is not particularly restricted insofar as it is sufficient to prevent and control the various manifestations of osteoporosis and climacteric disturbances accompanying malaise and/or menopause in middle-aged and elderly women. As a rule of thumb, however, the dosage can be generally selected so that the amount of equol excreted in the urine of the person who has taken the composition of the invention reaches at least 5 µmole (about 1.2 mg)/day.

BEST MODE FOR CARRYING OUT THE INVENTION

Figure 1:
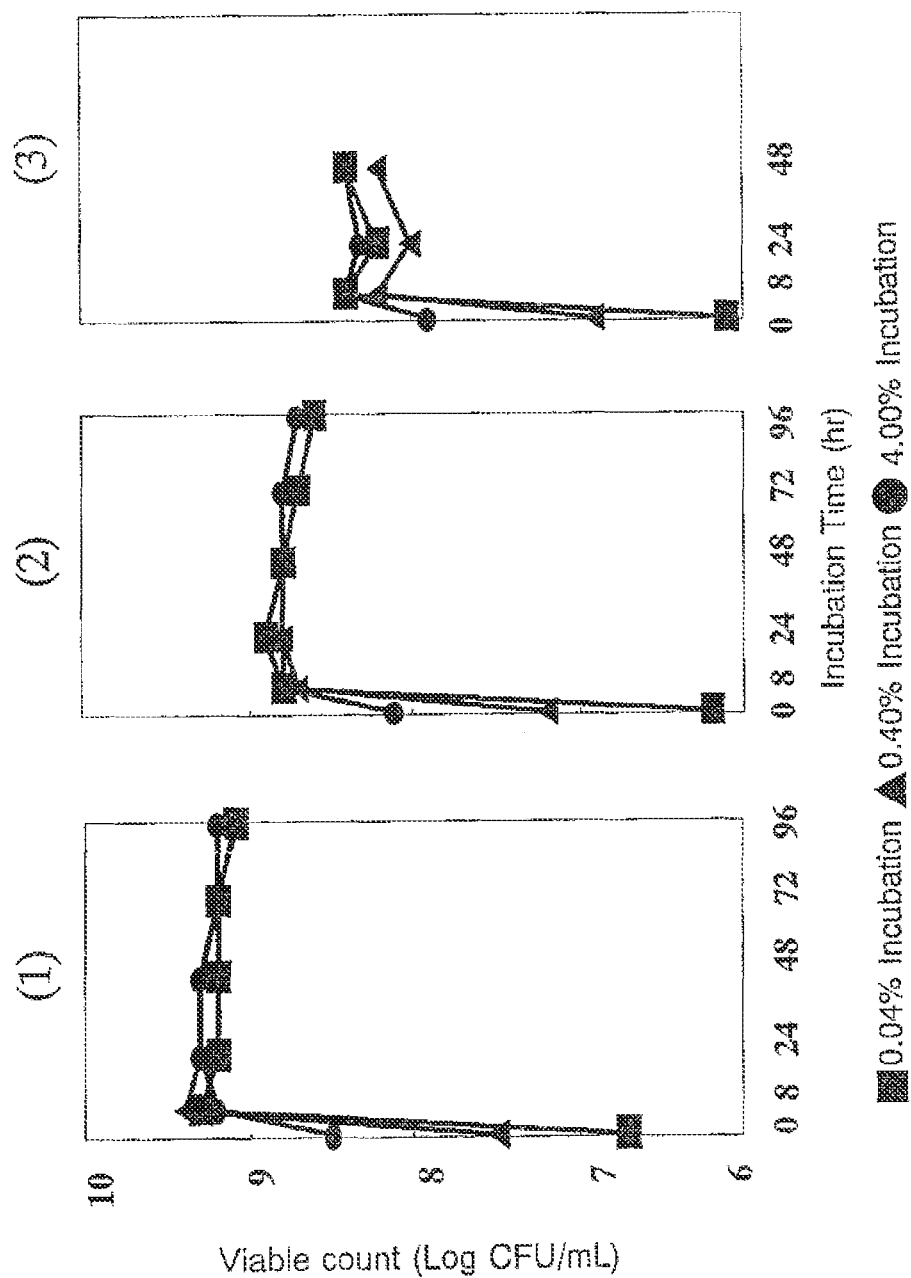
FIG. 1 is a diagrammatic representation showing the relationship of incubation time to viable cell count as determined by the test protocol described in Test Example 1.

The following examples of production of the equol-producing lactic acid bacteria-containing composition of the invention are intended to describe the present invention in further detail and should by no means be construed as defining the invention.

EXAMPLE 1

(1) Production of a Fermented Soy Milk Beverage

The following ingredients were taken according to the formula and blended to prepare the composition of the invention in the form of a fermented soy milk beverage.

| Fermentation culture of water-soluble soy protein | 100 mL |
|---|---|
| Vitamins & minerals | q.s. |
| Flavoring | q.s. |
| Water | q.s |
| Total | 150 mL |

The above fermentative culture of water-soluble soy protein was obtained by dissolving 13 g of water-soluble soy protein in 100 ml of water, adding $10^8$-$10^9$ cells of *Lactococcus* 20-92 (FERM BP-10036), and carrying out fermentation at 37° C. for 24-48 hours. The water-soluble soy protein used contained about 1-2 mg, calculated as daidzein, of daidzein compounds in each one gram.

(2) Production of a Fermented Milk

The following ingredients were taken according to the formula and blended to prepare the composition of the invention in a fermented milk form.

| *Lactococcus* 20-92 fermented milk | 100 mL |
|---|---|
| Vitamins & minerals | q.s. |
| Flavoring | q.s. |
| Water | q.s. |
| Total | 150 mL |

The *Lactococcus* 20-92 fermented milk was obtained by adding $10^8$-$10^9$ cells of *Lactococcus* 20-92 (FERM BP-10036) to 1 L of cow's milk (having a nonfat milk solids content of 8.5% or greater and a milk fat content of 3.8% or greater) and carrying out fermentation at 37° C. for 24-48 hours.

(3) Production of a Freeze-dried Powder of Fermented Soy Milk

Using about $10^9$ cells of *Lactococcus* 20-92 (FERM BP-10036) and 100 g of soy milk (soy solids 10%, daidzein compound content 10-15 mg calculated as daidzein), lactic acid fermentation was carried out at 37° C. for 72-96 hours for the production of equol. This fermentation product was freeze-dried to prepare a powder. The equol content of the powder as determined by HPLC was 0.1-0.3 weight %.

The powder obtained above and various other ingredients were weighed out according to the following formula and blended to prepare the composition of the invention in the powder form (food form and pharmaceutical product form).

Freeze-dried powder of fermented soy milk 2.2 g (equol content 0.005 g)

| Excipient (corn starch) | 17 g |
|---|---|
| Vitamins & minerals | q.s. |
| Flavoring | q.s. |
| Total | 20 g |

(4) Production of a Powder

The following ingredients were weighed out according to the formula and blended to prepare the composition of the invention in a powder form (food form and pharmaceutical product form).

| Freeze-dried powder of *Lactococcus* 20-92 | 4.1 g |
|---|---|
| Excipient (lactose) | 1.0 g |
| Vitamins & minerals | q.s. |
| Flavoring | q.s. |
| Total | 20 g |

A freeze-dried powder of *Lactococcus* 20-92 was obtained by culturing *Lactococcus* 20-92 (FERM BP-10036) in a suitable liquid growth medium (MRS) (37° C., 24-48 hrs), harvesting and suspending grown cells in 10% skim milk, and lyophilizing the suspension. The cell content of the powder was $10^9$-$10^{10}$ cells/g.

The above powder may be made into a daidzein-containing powder by blending it further with 4.1 g of semi-purified soy isoflavine powder.

Intake of the daidzein-containing powder thus obtained results in the urinary equol excretions of about 5 μmoles (about 1.2 mg) per day, indicating clearly that the amount of equol corresponding to the above excretions can be produced in vivo.

(5) Production of Granules

The following ingredients were weighed out according to the formula and blended to prepare the composition of the invention in a granular form (food form and pharmaceutical product form).

| Semi-purified soy isoflavone powder | 4.1 g |
|---|---|
| Freeze-dried powder of *Lactococcus* 20-92 | 1.0 g |
| Sucrose acid ester | q.s. |
| Vitamins & minerals | q.s. |
| Flavoring | q.s. |
| Total | 20 g |

The freeze-dried powder of *Lactococcus* 20-92 used was the same as the one used above in (1).

Intake of the above composition results in the concurrent delivery of daidzein and equol-producing bacteria to the large intestine, thus enabling production of equol in the large intestine.

Test Examples relating to the equol-producing lactic acid bacterial strain of the invention are presented below.

TEST EXAMPLE 1

Test for Growth Performance, Equol-producing Ability (Activity), and Equol Output
(1) Test Protocol

*Lactococcus* 20-92 ($10^7$-$10^9$ cells/g) was incubated in 5 mL of BHI broth [a liquid medium for growth (basal medium)] anaerobically at 37° C. for 24 hours and the culture was diluted to $10^2$ and $10^4$ cells with the basal medium.

The culture obtained at completion of incubation and its dilutions prepared above were respectively taken, 0.2 mL each, and blended with 5 mL each of daidzein-supplemented basal medium (daidzein added to BHI broth at a final concentration of 10 μg/mL), cow's milk and soy milk, respectively, and cultured anaerobically at 37° C. The incubation time was set to 8, 24, 48, 72, and 96 hours in the case of 10 μg/mL daidzein-supplemented basal medium and soy milk, and 8, 24 and 48 hours in the case of cow's milk.

Before the start of incubation and at the end of each incubation period, 0.1 mL and 0.2 mL portions of the culture were sampled and respectively subjected to the counting of cells and assay of equol-producing ability (activity). Furthermore, for 10 μg/mL daidzein-containing basal medium and soy milk, 0.5 mL of each culture was sampled before the start of incubation and at the end of each incubation period and the amount of equol produced in each sample was determined.

The number of bacteria was determined in the following manner. Each 0.1 mL sample was diluted with PBS(-) (product of Nissui Co.) to prepare $10^4$, $10^5$, $10^6$ and $10^7$-fold dilutions and 0.1 mL each of these dilutions were respectively coated on GAM agar medium and incubated aerobically at 37° C. for 24 hours. The colonies formed on the medium were counted for use as the number of bacteria.

The equol-producing ability (activity) was assayed as follows. Each 0.2 mL sample was blended with 5 mL of daidzein-supplemented basal medium (each in triplicate) and incubated anaerobically at 37° C. for 96 hours. At completion of incubation, 0.5 mL samples of the respective cultures were taken and respectively extracted twice with 5 mL portions of ethyl acetate and the daidzein, dihydrodaidzein (intermediate), and equol in the extract were quantitated by HPLC. Moreover, based on the total amount, the percentage of equol was calculated. The results were scored on the following 5-point scale and the average score of 3 samples was used as an index of equol-producing ability (activity).

4: Equol (90% or greater)
3: Equol produced, with daidzein diminishing to less than 50% (formation of intermediate)
2: Equol produced, residual daidzein (50% or greater) (formation of intermediate)
1: Intermediate formed, equol not produced
0: Neither intermediate nor equol produced, with daidzein not diminishing The amount of equol produced was determined as follows. Each 0.5 mL sample was extracted twice with 5 mL portions of ethyl acetate and the amounts of daidzein, dihydrodaidzein (intermediate), and equol in the extract were quantitated by HPLC. Then, the respective concentrations were used to calculate the amount of equol produced.
(2) Test Results
(2-1) The Results of Counting of the Cells (Growth Performance) are Presented in FIG. 1.

In the diagrammatic representation, (1) represents the result obtained in the case where the daidzein-supplemented basal medium was used, (2) represents the result obtained in the case where soy milk was used, and (3) represents the result obtained when cow's milk was used. In each diagram, the horizontal axis represents incubation time (hr) and the vertical axis represents viable cell count (Log CFU/mL).

It can be seen from the respective diagrams, the growth performance of the strain of the invention is good and, regardless of the inoculum size used, the stationary phase of growth was invariably attained in 8 hours of incubation in all the daidzein-supplemented basal medium, soy milk and cow's milk. The viable cell count was found to be steady at $10^{9.1-9.4}$ CFU/mL in the daidzein-supplemented basal medium, $10^{8.5-8.7}$ CFU/mL in soy milk, and $10^{8.0-8.4}$ CFU/mL in cow's milk.
(2-2) The Equol-producing Ability (Activity) Values Found are Presented in FIG. 2.

Figure 2:
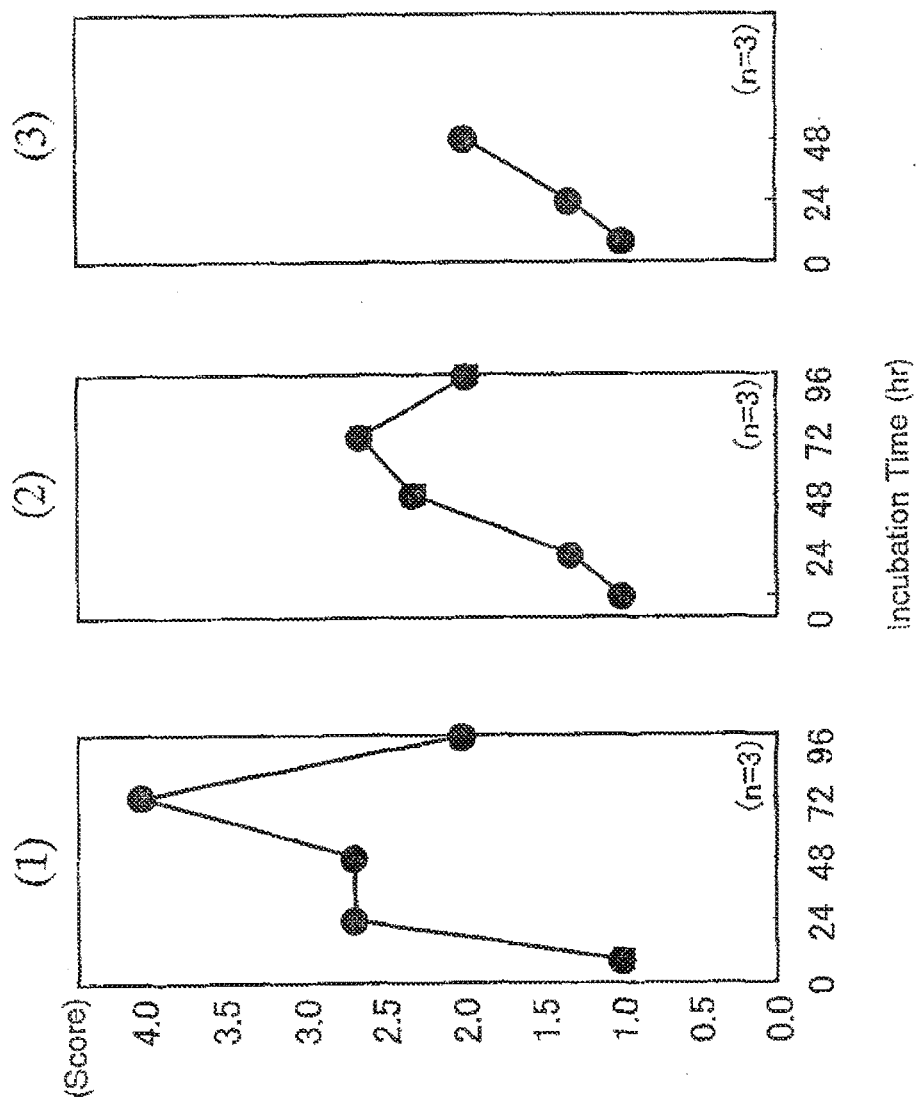
FIG. 2 is a diagrammatic representation showing the relationship of incubation time to equol-producing ability (score) as determined by the test protocol described in Test Example 1.

In FIG. 2, (1) represents the result obtained in the case where the daidzein-supplemented basal medium was used, (2) represents the result obtained in the case where soy milk was used, and (3) represents the result obtained in the case where cow's milk was used. In each diagram, the horizontal axis represents incubation time (hr) and the vertical axis represents activity score.

It is obvious from the results presented in FIG. 2 that the equol-producing ability (activity) tends to increase with time in any of the daidzein-supplemented basal medium, soy milk, and cow's milk. It could also be confirmed that even in the cases where cow's milk and soy milk were used, the equol-producing ability (activity) of the strain of the invention is sustained.
(2-3) Results of the Amount of Equol Produced Determination The quantities of equol produced in the daidzein-supplemented basal medium and soy milk (about 80 μg/mL calculated as daidzein) were as shown in FIG. 3.

Figure 3:
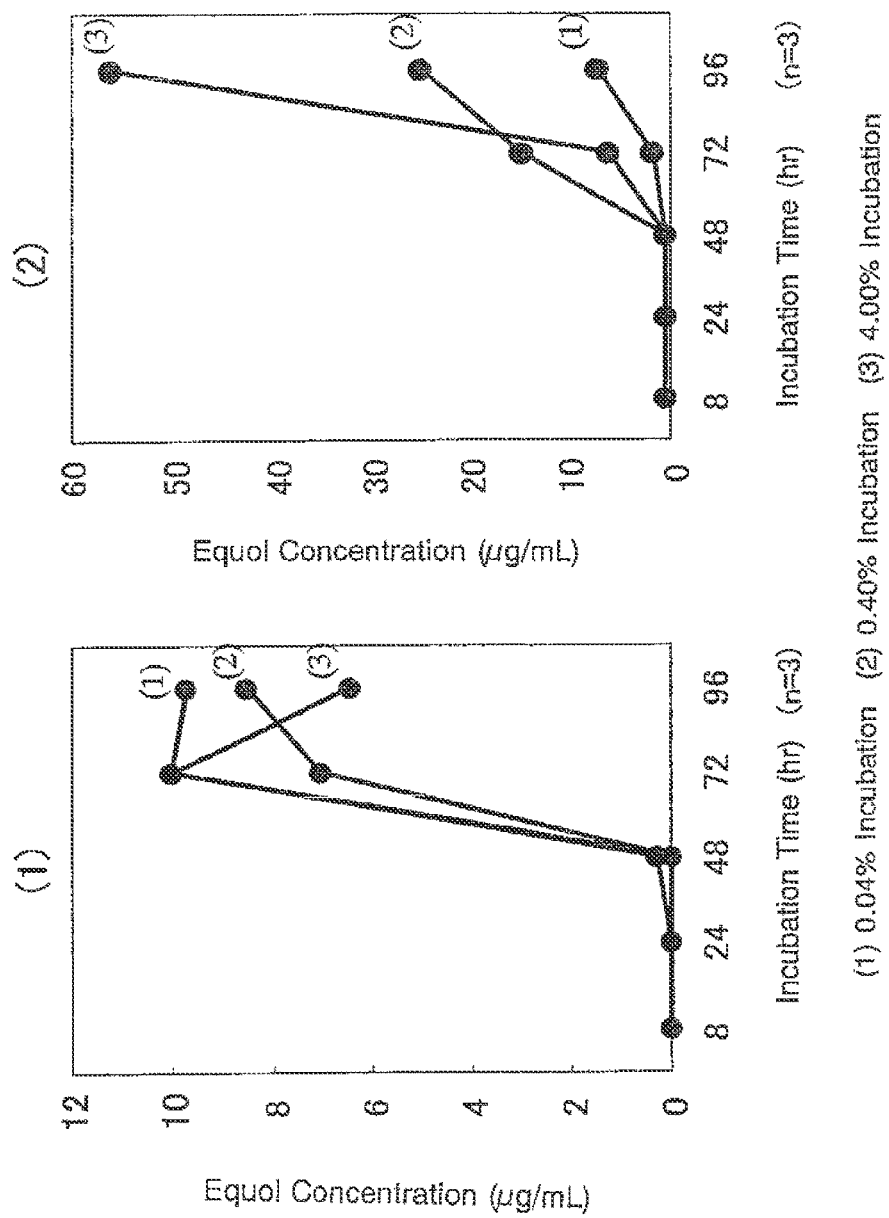
FIG. 3 is a diagrammatic representation showing the relationship of incubation time to equol output as determined by the test protocol described in Test Example 1.

Referring to FIG. 3, (1) represents the result obtained in the case where the daidzein-supplemented basal medium was used and (2) represents the result obtained in the case where soy milk was used. In each diagram, the horizontal axis represents incubation time (hr) and the vertical axis represents equol concentration (μg/mL).

In both media, the production of equol began to be noticed at hour-48 following the start of incubation. In the case where soy milk was used, the amount of equol produced varied with inoculum size and particularly at the inoculation level of 4.00%, the production of equol was as large as 57.0 μg/mL at hour-96 of incubation.

Although, in soy milk, not less than 90% of daidzein serving as the precursor of equol is present in the form of glycoside (in the form of glucose attached), the peak corresponding to the glycoside was no longer observed on the post-incubation chromatogram and this fact suggests that the strain of the invention decomposes the glycoside (β-glucosidase activity) to give daidzein and further metabolizes this daidzein to equol.

TEST EXAMPLE 2

Equol Production Pathway in *Lactococcus* 20-92
(1) Test Protocol
*Lactococcus* 20-92 ($10^7$ cells/mL) was aerobically cultured in 5 mL of BHI broth (a liquid medium for growth, basal medium) at 37° C. for 24 hours and 0.2 mL of the resulting culture was blended with 5 mL of daidzein-supplemented basal medium and the mixture was incubated anaerobically at 37° C. The incubation time was set to 8 hr, 24 hr, 30 hr, 36 hr, 48 hr, 51 hr, 54 hr, 60 hr, 84 hr, and 96 hr.

Figure 4:
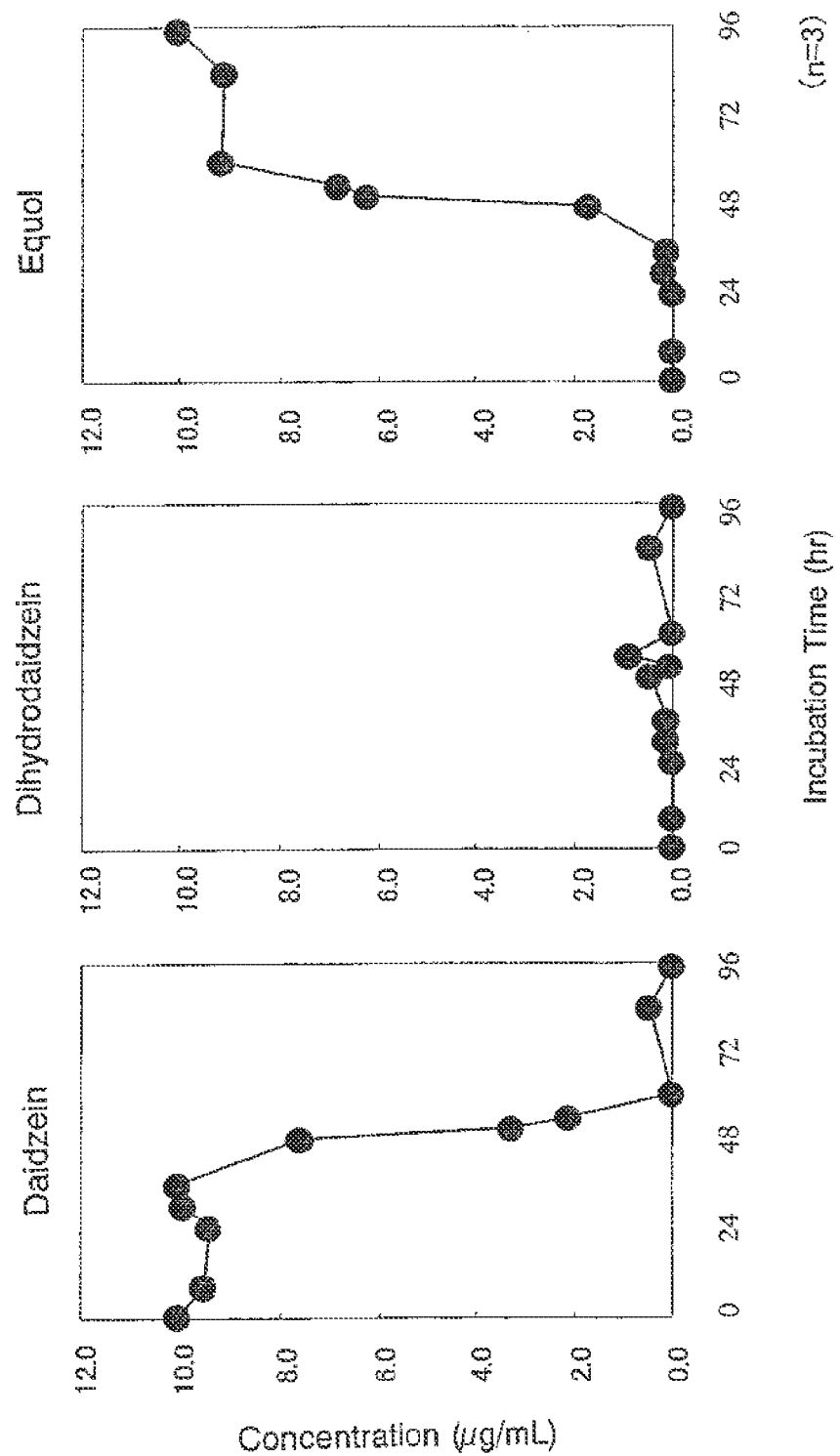
FIG. 4 is a diagrammatic representation showing the time course of concentration of each of daidzein compounds and equol in the culture as monitored in accordance with the protocol described in Test Example 2.

Before the start of incubation and at the end of each incubation period, 0.5 mL samples were taken and the concentrations of daidzein, dihydrodaidzein (intermediate), and equol in each sample were determined.
(2) Results
The results obtained are presented in FIG. 4.
FIG. 4 is a diagrammatic representation of the changes with time in the concentrations of daidzein (left), dihydrodaidzein (center), and equol (right). In each diagram, the horizontal axis represents incubation time (hr) and the vertical axis represents the concentration (μg/mL) of the corresponding substance.

It will be apparent from the data presented in FIG. 4 that the concentration of daidzein began to decline at hour-48 of incubation, the intermediate compound dihydrodaidzein was formed during the period from hour-48 to hour-60, and the production of equol began at hour-48. It can also be confirmed that the metabolism of daidzein to equol had substantially gone to completion by hour-60.

While the above results indicated that the metabolism from daidzein to equol occurred via said intermediate compound dihydrodaidzein, the results also suggested that the formation of dihydrodaidzein and the metabolism thereof to equol took place in parallel.

TEST EXAMPLE 3

Low-Temperature Stability of *Lactococcus* 20-92 Strain-containing Fermented Milks
(1) Test Protocol
*Lactococcus* 20-92 was cultured in 5 mL of a liquid medium for growth (basal medium) anaerobically at 37° C. for 24 hours, the resulting culture was used to inoculate 1 L and 2 L of cow's milk and 1 L of commercial skim milk (10% solids), respectively, at the level of 4% and cultured aerobically under stationary conditions at 37° C. for 48 hours. The cultures were stored at 4° C.

In the case of cow's milk, the equol-producing ability (activity) was monitored on a weekly basis following completion of culture through week 4 of low-temperature storage at 4° C. Furthermore, two of the tubes were reserved and stored till day-42 and day-51, respectively, and the activity was determined in each case.

In the case of skim milk, the activity was determined at completion of culture and at week-1 and day-34 of low-temperature storage at 4° C.

Figure 5:
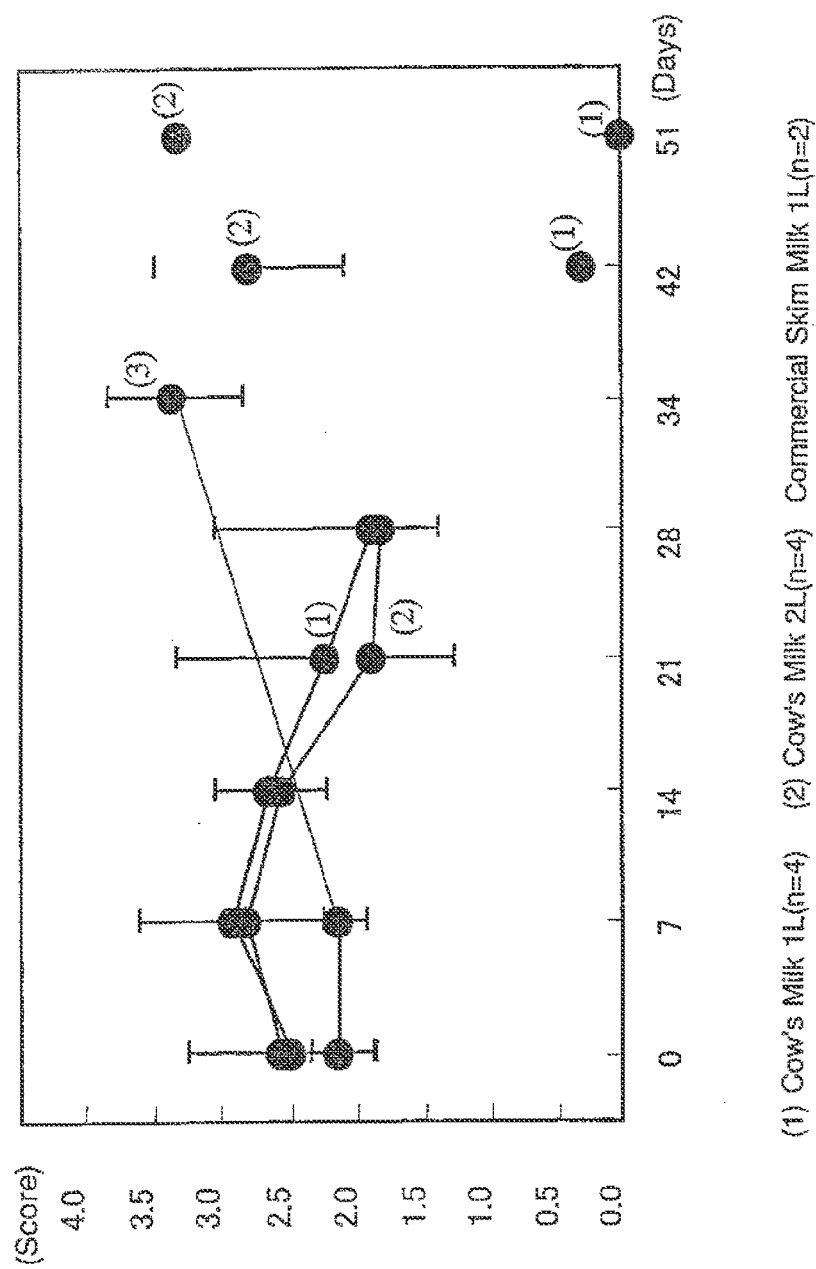
FIG. 5 is a diagrammatic representation showing the relationship of storage period to equol-producing ability (score) as determined in accordance with the test protocol described in Test Example 3.

The activity scores before storage and at the end of each storage period were generated by the above-described method comprising inoculating 5 mL of 10 μg/mL daidzein-supplemented basal medium at the level of 4% (0.2 mL) in triplicate, culturing the microorganism anaerobically at 37° C. for 96 hours, and determining the concentrations of daidzein, dihydrodaidzein (intermediate), and equol for activity scoring.
(2) Results
The results are presented in FIG. 5. In FIG. 5, the horizontal axis represents storage period (days) and the vertical axis represents activity score.

It is apparent from this diagrammatic representation of results that, as far as cow' milk is concerned, the equol-producing ability (activity) is sustained to week-4 of low-temperature storage at 4° C. after completion of culture in both cases of 1 L and 2 L. Moreover, in the case of 2 L of cow's milk, the activity was found to be sustained to day-51, that was the last day of monitoring of the storage stability at 4° C. In the case of 1 L of commercial skim milk, too, the equol-producing ability (activity) was apparently sustained to day-34, the last day of monitoring of the low-temperature storage stability at 4° C. after completion of culture.

The foregoing results indicate that the fermented milk prepared by using *Lactococcus* 20-92 is capable of retaining the activity even under low-temperature storage conditions and, therefore, is also suitable for food distribution.

Figure 6:
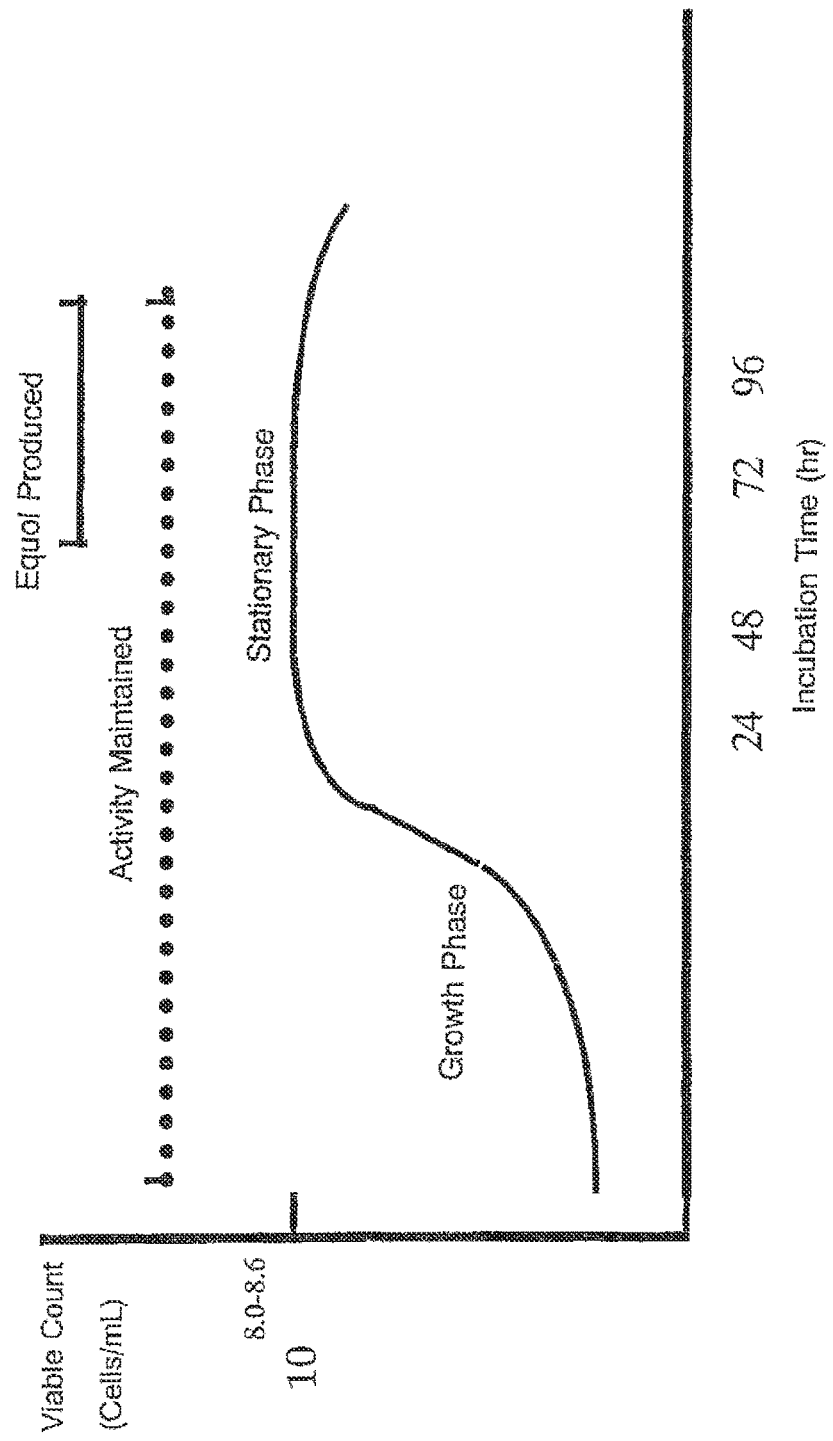
FIG. 6 is a diagrammatic representation showing the incubation time-dependent behaviors of the equol-producing strain (changes in growth performance, equol-producing ability, and equol output) as determined by the experiment described in Test Example 1-3.

The relationship of the growth performance of *Lactococcus* 20-92 to its equol-producing ability (activity) and the amount of equol produced as deducible from the results obtained in the above Test Examples 1-3 can be diagrammatically represented as shown in FIG. 6.

Thus, although cultural conditions varied with different culture media, the equol-producing ability (activity) can be maintained in both the growth phase and the stationary phase. On the other hand, with regard of equol output, it appears that the enzyme begins to, be expressed or activated to produce equol after a certain lag time in the stationary phase.

TEST EXAMPLE 4

Gastric Juice Tolerance Test of the Fermented Milk Prepared by using *Lactococcus* 20-92
(1) Test Protocol
*Lactococcus* 20-92 was anaerobically cultured in 5 mL of a liquid medium for anaerobic growth (BHI broth, basal medium) at 37° C. for 24 hours. The resulting culture ($10^9$ cells/g) was used to inoculate 1 L of cow's milk at the 4% level and incubated aerobically under stationary conditions at 37° C. for 48 hours. After completion of culture, the milk was stored at 4° C. and, regarding it as fermented milk, was subjected to the following test.

As artificial gastric juices, 0.045% pepsin-supplemented 50 mM glycine-HCl buffers (pH 2.5 and pH 3.0) were prepared. As control, 50 mM glycine-HCl buffer (pH 6.0) was prepared.

To 9 mL of each artificial gastric juice, 1 mL of the fermented milk stored at low temperature was added and the mixture was incubated (cultured) aerobically under stationary conditions in an incubator at 37° C.

The incubation time was set to 1 hr, 2 hr, and 3 hr, and 0.1 mL and 0.2 mL aliquots of each culture were respectively sampled before the start of incubation and at the end of each incubation period and subjected to the determination of viable cell count (in the case of 0.1 mL) and equol-producing ability (activity) (in the case of 0.2 mL).

The determination of viable cell count was carried out in accordance with the procedure described above in Test Example 1-(1), which comprises sampling 0.1 mL of each culture, diluting the sample $10^4$, $10^5$, $10^6$ and $10^7$-fold with Nissui's PBS(−), coating 0.1 mL of each dilution on GAM agar medium, incubating the inoculated medium aerobically at 37° C. for 24 hours, and counting the colonies formed on the GAM agar.

The determination of equol-producing ability (activity) was carried out in accordance with the procedure described above in Test Example 1-(1), which comprises inoculating 5 mL of daidzein-supplemented basal medium with 0.2 mL (4%) of the sample (in triplicate), incubating the inoculated medium anaerobically at 37° C. for 96 hours, and measuring the concentrations of daidzein, dihydrodaidzein (intermediate), and equol in the medium for activity scoring.

(2) Results

Figure 7:
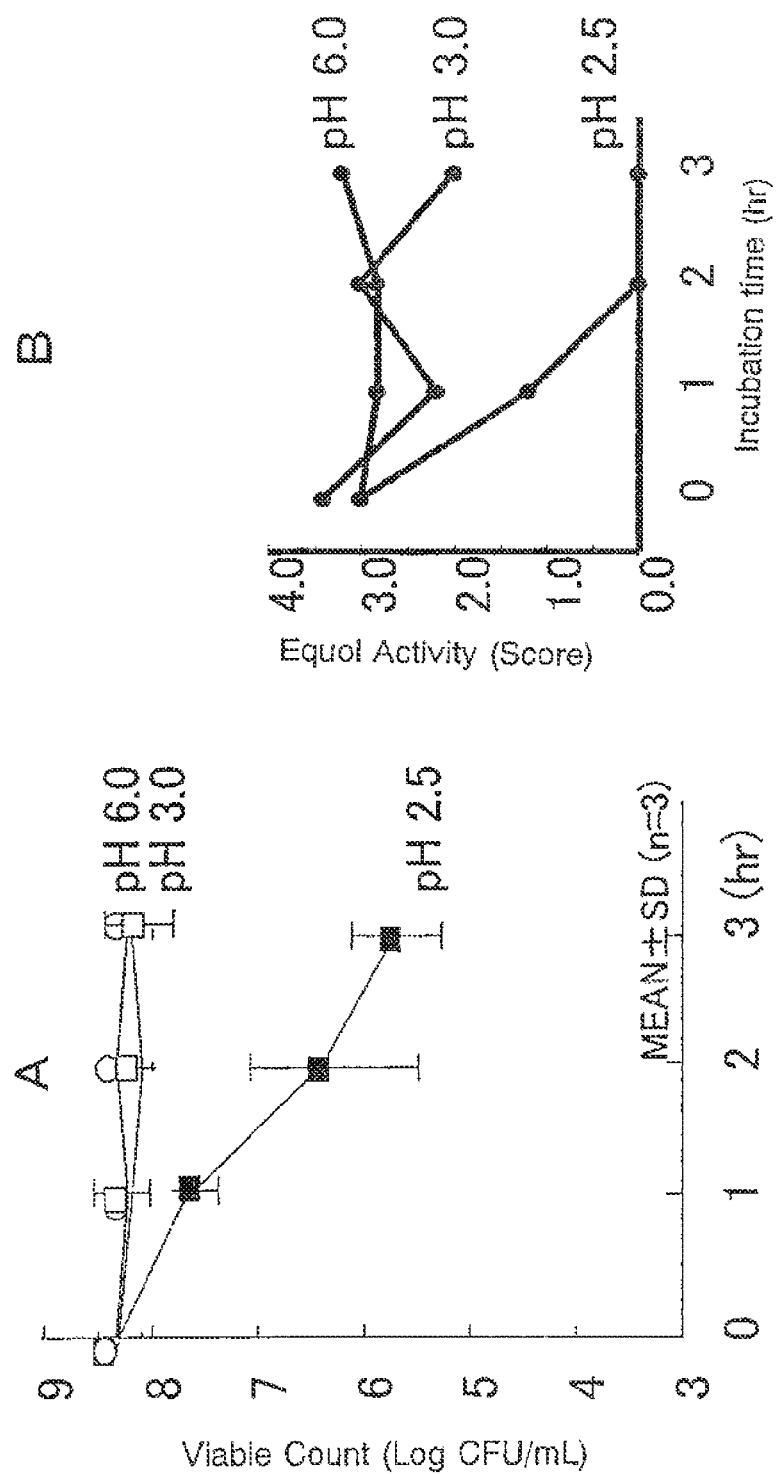
FIG. 7 is a diagrammatic representation showing the relationship of incubation time to viable cell count as determined by the test protocol described in Test Example 4.

The results obtained are presented in FIG. 7-A (viable cell count) and B (equol concentration).

In FIG. 7-A, the horizontal axis represents incubation time (hr) and the vertical axis represents viable cell count (Log CFU/ml in milk).

In FIG. 7-B, the horizontal axis represents incubation time (hr) and the vertical axis represents equol activity (score).

The following can be deduced from the results presented in FIGS. 7-A and 7-B. Thus, in the buffer solution at pH 6.0, the viable cell count was sustained at the $10^8$ cells/mL level up to hour-3, and, here, the equol-producing ability (activity) was also sustained. In the artificial gastric juice at pH 3.0, the viable cell count was sustained up to hour-3 of incubation and, here, the activity was also sustained. On the other hand, in the artificial gastric juice at pH 2.5, a marked decrease in viable cell count began to take place at hour-2 of incubation and the activity also disappeared.

When studied in the same test system as above, the probiotics (microorganisms which find their way alive into the intestinal canal and exhibit physiological activity there) on the market are reportedly unchanged in viable cell count at pH 3.0 but decreased significantly at pH 2.5. This means that the tolerance to gastric juice at pH 3.0 allows these microorganisms to pass through the stomach alive. Therefore, the fermented milk prepared by using *Lactococcus* 20-92 is reasonably expected to deliver the organisms alive to the intestines to let them exhibit sustained activity in the lower part of the small intestine and in the large intestine.

TEST EXAMPLE 5

Bile Tolerance Test of *Lactococcus* 20-92

The tolerance to bile was determined with VITEK GPI Card (Nippon Biomérieux Co., Ltd) and evaluated by using the growth performances of the strain of the invention in 10% and 40% biles as indicators.

(1) Test Protocol

*Lactococcus* 20-92 ($10^{8-9}$ cells) was smeared on 5% sheep blood-supplemented Trypticase-Soy agar and aerobically cultured at 37° C. for 24 hours. The colonies on the medium at completion of culture were hooked with a platinum loop and a homogeneous suspension thereof in 0.5% sterile saline was prepared. This suspension was placed in VITEK GPI Card and, after 15 hours' incubation at 35° C., the growth performance of the strain in the presence of bile was evaluated by using the dye (pH indicator). The bile was prepared by dissolving a predetermined amount of bile powder in sterile distilled water and placed in the Card in advance.

(2) Results

The results of the above test indicate that *Lactococcus* 20-92 grows in 10% and 40% biles, showing tolerance to 40% bile.

TEST EXAMPLE 6

Hemolysis Test of *Lactococcus* 20-92

(1) Test Protocol

*Lactococcus* 20-92 ($10^{8-9}$ cells) was smeared on 5% sheep blood-supplemented Trypticase Soy agar and cultured anaerobically ($N_2:CO_2:H_2=8:1:1$) at 37° C. for 24-48 hours. The portion around the colony formed on the medium after completion of culture was observed, and the hemolytic potential was evaluated according to the extent of decomposition of blood components (depigmentation or discoloration).

(2) Results

As the result of the above test, depigmentation (appearance of a transparent, colorless zone) was not observed around the colony, indicating that *Lactococcus* 20-92 does not cause β-hemolysis and, in this respect, is a safe microorganism.

TEST EXAMPLE 7

Cell-infiltrating Enzyme Activity Test of *Lactococcus* 20-92

Regarding the systemic invasion of ingested lactic acid bacteria, a depression in the defensive function of the mesenterium or impairment of the mesenterium itself may be considered as the factor on the host side. As the factor on the side of bacteria, their enzymatic activity (cell-infiltrating enzymes) decomposing the lipid-protein complex proteoglycans constituting the mesenterium can be mentioned.

This test was intended to investigate whether *Lactococcus* 20-92 has cell-infiltrating enzyme activities, namely collagenase (gelatinase), hyaluronidase and sialidase (neuraminidase) activities, or not and was carried out in the following manner.

(1) Test Protocol

*Lactococcus* 20-92 was smeared (smear size: $10^{8-9}$ cells) on blood-supplemented agar medium and cultured anaerobically ($N_2:CO_2:H_2=8:1:1$) at 37° C. for 24-48 hours.

The colonies on the medium after culture were hooked up with a platinum loop and suspended in sterile distilled water to prepare a homogeneous suspension. Using this suspension, the presence or absence of collagenase (gelatinase) was investigated with Api™ (Nippon Biomérieux Co., Ltd.) using the degradation of gelatin as the indicator.

Moreover, the test as to whether *Lactococcus* 20-92 has hyaluronidase and sialidase (neuraminidase) activities or not was carried out by the procedure comprising incubating *Lactococcus* 20-92 in Tris-HCl buffer solution (pH 7.0) containing hyaluronic acid or sialic acid as the substrate (37° C., aerobic, 15 min. for sialidase activity and 24 hr for hyaluronidase activity) and measuring the degrees of decrease in the concentrations of the respective substrates.

(2) Results

*Lactococcus* 20-92 showed none of collagenase (gelatinase), hyaluronidase, and sialidase (neuraminidase) activities.

Thus, in view of the fact that the strain of the invention lacks cell-infiltrating enzymes which constitute a factor in infectivity, the strain was confirmed to be a highly safe microorganism from infectivity points of view as well.

TEST EXAMPLE 8

Vancomycin Resistance Test

The acquisition of resistance to antibiotics (mutation) by bacteria has been a matter of serious concern in recent years. It is not rare that patients infected with bacteria which have acquired such resistance to antibiotics succumb to death because they do not respond to the antibiotics. Particularly, the emergence of vancomycin-resistant bacteria (VRE) is a matter of serious concern in the field of clinical medicine today. Moreover, there is the apprehension that if the ingested organisms harboring the vancomycin resistance gene reach and settle in the intestines where they come into contact with virulent or infectious microorganisms (pathogenic bacteria), the vancomycin resistance gene may be transferred to the pathogenic bacteria, with the result that these bacteria also acquire vancomycin resistance. Therefore, it is necessary, at least, that microorganisms which are used as probiotics should not be vancomycin-resistant organisms.

This test was intended to investigate the susceptibility of *Lactococcus* 20-92 to vancomycin and was performed as follows.

(1) Test Protocol

The vancomycin susceptibility test was performed using Sensi-Disk (product of Nippon Becton-Dickinson Company, Ltd.). *Lactococcus* 20-92 was smeared (smear size: $10^{8-9}$ cells) on GAM agar medium, a disk containing 30 μg of vancomycin was placed on the medium, and an aerobic culture was carried out at 37° C. for 24 hours. After the above incubation time, the diameter of the inhibition zone formed around the disk was measured and evaluated according to the evaluation table.

(2) Results

The diameter of the inhibition zone for *Lactococcus* 20-92 was 11.9±0.2 mm and the susceptibility evaluation according to the evaluation table was positive (susceptible: =10 mm). This result indicated that the strain of the invention is not a vancomycin-resistant strain and, therefore, is considered safe.

Presented in Example 2 below is an example of the production of equol from daidzein by using the lactic acid bacterial strain of the invention.

EXAMPLE 2

Production of Equol

One mL of suspension containing $10^7$-$10^9$ cells of *Lactococcus* 20-92 (FERM BP-10036) in GAM medium for culture of anerobic bacteria was prepared and this suspension was added to 100 g of soy milk (solids concentration: ca 2.2%). The mixture was incubated anaerobically at 37° C. for 72-96 hours and the equol produced in the culture was monitored by HPLC. The daidzein compound content of said soy milk was 95 μg/mL calculated as daidzein.

The result indicated the formation of 10.7±6.3 μg/mL (mean±standard deviation of 3 experiments) of equol in the above soy milk culture.

The above finding shows clearly that by exploiting the microorganism of the invention, equol can be produced from the daidzein compounds contained in food materials with good efficiency and at low cost.

The invention claimed is:

1. An isolated strain of *Lactococcus garvieae* 20-92 deposited under accession number FERM BP-10036, wherein said strain is in a lyophilized form.

2. A composition comprising the lyophilized strain of claim 1.

3. A composition comprising *Lactococcus garvieae* 20-92 deposited under accession number FERM BP-10036, wherein said composition is in the form of fermented milk or fermented soy milk, said fermented milk or fermented soy milk having been fermented by said *Lactococcus garvieae* 20-92.

* * * * *